(12) United States Patent
Quellet et al.

(10) Patent No.: US 10,426,131 B2
(45) Date of Patent: *Oct. 1, 2019

(54) FRAGRANCE COMPOSITION

(71) Applicant: GIVAUDAN SA, Vernier (CH)

(72) Inventors: Christian Quellet, Biel (CH); Johnny Bouwmeesters, Oetwil Am See (CH); Sibilla Delorenzi, Zurich (CH); Thomas McGee, Nyack, NY (US)

(73) Assignee: GIVAUDAN S.A., Vernier (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/813,238

(22) Filed: Nov. 15, 2017

(65) Prior Publication Data

US 2018/0070555 A1    Mar. 15, 2018

Related U.S. Application Data

(63) Continuation of application No. 11/909,662, filed as application No. PCT/CH2006/000187 on Apr. 3, 2006, now Pat. No. 10,004,205.

(51) Int. Cl.
| | |
|---|---|
| *A61L 9/04* | (2006.01) |
| *A61K 8/00* | (2006.01) |
| *A01K 1/015* | (2006.01) |
| *A61L 9/01* | (2006.01) |
| *A61L 9/014* | (2006.01) |

(52) U.S. Cl.
CPC ............ *A01K 1/0152* (2013.01); *A61L 9/01* (2013.01); *A61L 9/014* (2013.01)

(58) Field of Classification Search
CPC .......... A01K 1/0152; A61L 9/01; A61L 9/014
USPC ......................................... 512/4, 1
See application file for complete search history.

(56) References Cited

U.S. PATENT DOCUMENTS

| | | | |
|---|---|---|---|
| 3,971,852 A | 7/1976 | Brenner et al. | |
| 4,407,231 A * | 10/1983 | Colborn | A01K 1/0152 |
| | | | 119/171 |
| 4,842,761 A | 6/1989 | Rutherford | |
| 5,290,547 A | 3/1994 | Bilbrey et al. | |
| 5,662,067 A | 9/1997 | Stubbs et al. | |
| 5,775,259 A | 7/1998 | Tucker et al. | |
| 6,287,550 B1 * | 9/2001 | Trinh | A01K 1/0152 |
| | | | 119/171 |
| 10,004,205 B2 * | 6/2018 | Quellet | A01K 1/0152 |
| 2002/0007800 A1 * | 1/2002 | Ochi | A01K 1/0155 |
| | | | 119/171 |
| 2003/0072733 A1 | 4/2003 | McGee et al. | |

FOREIGN PATENT DOCUMENTS

| | | | |
|---|---|---|---|
| EP | 0076122 A | 4/1983 | |
| EP | 1092346 A | 4/2001 | |
| FR | 2794994 A | 12/2000 | |
| JP | 2005021071 A | 12/2003 | |
| JP | 2004033047 A | 2/2004 | |
| WO | 0226272 A | 4/2002 | |

* cited by examiner

*Primary Examiner* — Jessica Whiteley
(74) *Attorney, Agent, or Firm* — Norris McLaughlin, PA

(57) ABSTRACT

A solid, free-flowing composition adapted to deliver fragrance or malodor counteractant in a consumer product that is subjected to actual or potential malodorous influences. The composition comprises a delivery system consisting of a core material surrounded by a fragranced material comprising microdroplets of a dispersed fragrance in a fragrance-encapsulating material, optionally surrounded by a protective coating, and, an external absorbent material in which the fragrance delivery vehicle is dispersed. The composition is effective with respect to animal litters.

20 Claims, No Drawings

FRAGRANCE COMPOSITION

This application is a continuation application of pending U.S. Ser. No. 11/909,662 filed on Sep. 25, 2017, which is a 371 application of PCT/CH2006/000187 filed Apr. 3, 2006, which claims the benefit of U.S. Provisional Application No. 60/668,176 filed Apr. 4, 2005.

This invention relates to an odour control composition that is capable of absorbing malodor and moisture and simultaneously releasing a fragrance in a controlled way, more particularly to such compositions for use in consumer products, especially solid consumer products for odour control such as sanitary products, diapers, pet litters, air fresheners, central air systems, humidity absorbers and the like.

Absorbent materials have traditionally been used to absorb malodors and moisture. In some cases, odor-counteracting compounds such as a chemically reactive substance, a masking scent or a pleasant fragrance is added directly to the absorbent. Adding malodor-counteracting compounds directly to absorbents has, however, severe drawbacks. Firstly, irreversible adsorption of part of the malodor-counteracting compound often alters the efficacy of the compound. Secondly, due to specific odorant-absorbent interactions, some components of the added fragrance may be more absorbed or retained than others within the pores of the absorbent, leading to distortion of the olfactive characteristics of the fragrance. Thirdly, adding odorants directly to absorbents usually leads to over-dosed olfactive impact of freshly prepared composition and under-dosed olfactive impact of aged composition. The release of the smell is, in the case in which the fragrance has been added directly to absorbent, essentially uncontrolled.

Furthermore, fragrances have been traditionally added to consumer products by mixing a liquid fragrance into the product. There are a number of problems with this approach, such as the possibility of unacceptably high fragrance loss during manufacture, uneven distribution of fragrance in the product, clogging of manufacturing machinery and poorer mechanical properties of the final product.

U.S. Pat. No. 6,803,833 discloses a process for releasing fragrance in the presence of absorbent materials by providing a delivery vehicle containing an enrobment material, a fragrance and a fixative, wherein the enrobment material is a powder material that is capable of absorbing oleophilic substances, and the fixative is a high molecular weight, low melting wax or solid, such as polyethylene glycol.

Although the process described in U.S. Pat. No. 6,803,833 certainly provides improved odor control compared to the prior art, it has the disadvantage of relying on a range of fixatives and enrobment materials that are not known to be highly efficient in retaining volatile fragrance ingredients over a prolonged period of time, especially at room temperature and above. Thus, it is expected that such fragrance delivery vehicles will lose their odor-control efficacy with time.

Spray drying of the fragrance in a soluble matrix, such as dextrin, maltodextrin and sugar, has been used to try to protect the fragrance. However, while this procedure has produced encapsulation, the resulting encapsulated form is invariably a fine powder, which is difficult to handle and to incorporate homogeneously in the product, and which is prone to attrition during processing of the product.

Furthermore, spray-dried fragranced particles are generally very sensitive to humidity, and exposure to moisture over a long period of time often results in fragrance losses and decreased olfactive performance.

Accordingly, there remains a need to provide an odor-control composition that is capable of absorbing malodor and moisture and simultaneously releasing a fragrance or volatile malodor-counteracting substances in a controlled way and which does not suffer from the drawbacks quoted above. In particular, there remains a need to provide an odor-control composition having the capability of retaining the fragrance or volatile malodor-counteracting substance over a prolonged period of time, even under drastic storage conditions such as temperatures exceeding 35° C. and relative humidity higher than 65%, while still releasing this fragrance in contact with aqueous liquids such as urine, refrigeration water, and the like.

It has now been found that the disadvantages of the known art can be substantially and even completely overcome by the use of a particular multifunctional odor-control composition. The invention therefore provides a solid, free-flowing composition adapted to deliver fragrance or malodor counteractant in a consumer product that is subjected to actual or potential malodorous influences, comprising:
a delivery system consisting of a core material surrounded by a fragranced material comprising microdroplets of a dispersed fragrance in a fragrance-encapsulating material, optionally surrounded by a protective coating, and,
an external absorbent material in which the fragrance delivery vehicle is dispersed.

In a particular embodiment of the invention, the composition consists essentially of a delivery system and an external absorbent material, as hereinabove defined.

In a particular embodiment of the invention, both delivery system and external absorbent materials are in free-flowing, granulated form. The external absorbent has a particle size ranging from 0.2 to 10 millimeters, and in particular 0.5 to 5 millimeters, whereas the delivery system has particle sizes preferably ranging from 0.5 to 4 millimeters, in particular from 1.5 to 3 millimeters and from 0.8 to 3 millimeters. These sorts of size ranges are particularly desired and one of the advantages of the present invention is that the particles of the delivery system may easily be made these sizes.

The shape of the particles is not critical. Although the particles of both delivery system and external absorbent are preferably essentially spherical, as such a shape is more attractive in appearance and particles of this shape are less prone to attrition during transport, it is possible for the particles of one or both of the delivery system and the external absorbent to have other shapes. Examples of other shapes include platelets (especially favoured for animal litters), crystals, cylinders, ellipsoids and fibres. In non-spherical cases, the dimensions hereinabove given refer to the major dimension of the particle.

In a most preferred embodiment of the invention, the delivery system and the external absorbent phase are of different colors.

The invention additionally comprises a method of reducing or eliminating malodor, comprising the contacting of an actual or potential source of malodor with a free-flowing solid malodor counteractant composition as hereinabove define.

By "core material" is meant a particulate material that is dispersed in or coated with a fragranced material, or coated with a fragrance-encapsulating material. The core material may absorb part of the fragrance included in the delivery system and facilitate its delayed release. The number and sizes of core material particles present are not narrowly critical, provided the particle size requirements of the final product are met. The core material may be any such material known to the art that can be produced at or reduced to the desired size for internal use in particles. It may be organic or inorganic. It is permissible to use a blend of two or more such absorbent materials.

The core material has, in one embodiment, a bulk density of from 0.2-2.0 g/cm$^3$, more particularly from 0.2-1.5 g/cm$^3$, 0.5-1.2 g/cm$^3$ and 0.8-1.2 g/cm$^3$.

Furthermore, the core material may be a water-soluble material or a water-insoluble absorbent material, or a mixture thereof. It will be obvious to a person skilled in the art, that, by varying the composition of the core material, it is possible to obtain core materials that are completely soluble in water, partially soluble or dispersible in water or completely insoluble in water, depending on the type of application envisioned and on the visual effect desired.

Examples of water-soluble core materials useful as core material in this invention include (but are not limited to) inorganic materials like salts of alkaline metals and alkaline earth metals, and organic materials like low molecular weight, non-cellulosic carbohydrate such as sucrose, fructose, saccharose, and other sugars, maltodextrins, and powders of water-soluble polymers such as polyvinyl alcohol, polystyrene sulfonate, polyacrylates and the like.

In a particular embodiment of the invention, the water-soluble core material is essentially at least one water-soluble sugar.

In a further embodiment, the core material consists essentially of a water-insoluble organic material. In a particular embodiment, the core material is of vegetal origin. In a further particular embodiment, the core material consists of corn cob. This embodiment is further discussed hereinunder.

Typical non-limiting examples of suitable water-insoluble absorbent materials include clays such as diatomaceous earth, sodium and calcium bentonites, sepiolites, illite and kaolinite; zeolites, aluminosilicates and porous or mesoporous silicates, silica gel, hydrated silicon dioxide, which may be modified by chemical treatment; organic materials such as ground corn cob, husks, wheat fibres and cellulose fibres.

In a further embodiment, the core material consists essentially of a water-insoluble absorbent material. In a more preferred embodiment the core material is an inorganic material. In an even more preferred embodiment, the core material is identical to the external absorbent material. This embodiment is further discussed hereinunder.

Fragrance materials for use in compositions of the present invention may be selected from natural products such as essential oils, absolutes, resinoids, resins, concretes, and synthetic perfume components such as hydrocarbons, alcohols, aldehydes, ketones, ethers, acids, acetals, ketals and nitriles, including saturated and unsaturated compounds, aliphatic, carbocyclic and heterocyclic compounds, or precursors of any of the above. Other examples of odorant compositions which may be used are described in H 1468 (United States Statutory Invention Registration). The fragrance may optionally have aroma chemicals that are know to reduce the perception of malodors. The fragrance may optionally have aroma chemicals that are known to reduce the perception of malodors and/or prevent their formation via antimicrobial action.

Non-limiting examples of malodor counteractants include aldehydes such as trimethyl hexanal, benzaldehyde, vanillin, lyral, methyl dihydro jasmonate, ligustral, melonal, octyl aldehyde, citral, cymal, nonyl aldehyde, bourgeonal, lauric aldehyde; enones such as ionone alpha, ionone beta, ionone gamma methyl, alcohols such as cycloalkyl tertiary alcohol, cyclohexyl-2-methyl-2-butanol, cyclohexyl-1-ethanol; ketones such as 4-ethylcyclohexyl methyl ketone, 3, and 4-isopropylcyclohexyl methyl ketone and 4-cyclohexyl-4-methyl-2-pentanone; esters such as geranyl crotonate, cyclohexyl-1-ethyl-n-butyrate, cyclohexyl-1-ethyl-acetate, 2-hydroxyethyl p-tert-butylphenoxyacetate, 6-hydroxylhexyl phenoxyacetate, 4-hydroxybutyl phenoxyacetate, benzyl cinnamate, octyl methoxy cinnamate, phenyl cinnamate, fumaric acid esters, 2-hydroxyethyl phenoxyacetate, 2-hydroxyethyl p-tert-butylphenoxyacetate, 6-hydroxylhexyl phenoxyacetate, 4-hydroxybutyl phenoxyacetate, methyl and ethyl esters of 3-methyl-2-hexenoic acid , cyclohexyl-methyl and cyclohexenylmethyl; carbonates such as isocyclogeraniol carbonates, cyclohexene carbonates, cyclohexane carbonates, norbornene carbonates, and dihydroisocyclogeraniol carbonates; nitiles, such as 3-methyl-5-phenyl-pentanenitrile and 3-methyl-5-cyclohexyl-pentanenitrile and their mixtures.

Non-limiting examples of antimicrobial materials include cyclic alcohols, for example, 3-phenyl-2-propen-1-ol, 4-(1-methylethyl)-benzene methanol, 2-phenyl-ethanol, 3-phenyl-propanol benzyl alcohol, phenyl ethyl alcohol; branched or unbranched linear alcohols, for example, from 10-undecenol, 1-nonanol, lactones, for example, 5-hexyl-furan-2 (3h)-one, dihydro-5-pentyl-2(3h)-furanone, cyclic ethers such as 2,4,4'-trichloro-2-hydroxy-diphenyl ether; phenolic compounds, such as phenol, 2-methyl phenol, 4-ethyl phenol; essential oils such as rosemary, thyme, lavender, eugenol, geranium, tea tree, clove, lemon grass, peppermint, anise, lemons, oranges, sandalwood, cedar, vervaine, or their active components such as anethole, thymol, eucalyptol, eugenol, farnesol, menthol, limonene, methyl salicylate, salicylic acid, terpineol, nerolidol, geraniol, cedrol, cavacrol, verbenone, eucalyptol and pinocarvone, hinokitiol, berberine, cinnamic aldehyde, cinnamyl alcohol and mixtures thereof; cyclic aldehydes, for example, 2-methyl-3-phenyl-2-propenal, 2-phenyl-propanal, branched or unbranched linear aldehydes, for example, 3,7-dimethyl-octa-2,6-dien-1-al, 2,4-nonadienal; and their mixtures thereof.

Fragrance materials particularly suitable for use with the present invention are those having a loss factor lower than $10^4$ Pa ppm, wherein the term "Loss Factor" refers to a parameter that is related to the losses of fragrance material during agglomeration in a fluidized bed and is defined as the product of the pure component saturation vapour pressure (Pa) in the standard state (278.15 K, 1 atm) and the water solubility (ppm) at room temperature. Vapour pressures and water solubility data for commercially-available fragrance components are well known and so the Loss Factor for a given fragrance component may be easily calculated. Alternatively, vapour pressure and water solubility measurements may be easily taken using techniques well known in the art. Vapour pressure of fragrance components may be measured using any of the known quantitative headspace analysis techniques, see for example Mueller and Lamparsky in "Perfumes: Art, Science and Technology", Chapter 6 "The Measurement of Odors" at pages 176-179 (Elsevier 1991). The water solubility of fragrances may be measured according to techniques known in the art for the measurement of sparingly water-soluble materials. A preferred technique involves the formation of a saturated solution of a fragrance component in water. A tube with a dialysed membrane is placed in the solution such that after equilibration an idealised solution is formed within the tube. The tube may be removed and the water solution therein extracted with a suitable organic solvent to remove the fragrance component. Finally the extracted fragrance component may be concentrated and measured, for example using gas chromatography.

Other methods of measuring fragrances are disclosed in Gygax et al, Chimia 55 (2001) 401-405.

By "fragrance-encapsulating material" is meant a barrier material effectively preventing the fragrance from diffusing out of the delivery system. Fragrance-encapsulating materials are hydrophilic materials that may be selected from:
(1) water-soluble or water-dispersible polymer, especially polysaccharides and modified polysaccharides, such as starch and modified starch or dextrin bearing octenyl succinate moieties;
(2) maltodextrin, sugars, sugar alcohols, mannitol, inulin, and trehalose;
(3) natural or synthetic gums such as alginate esters, gum arabic, gum tragacanth and gum karaya, carrageenan, xanthanes, agar-agar, pectines, and pectic acid;
(4) synthetic water-soluble or partially water-soluble, or -degradable polymers, such as (i) vinyl polymers such as poly(vinyl alcohol), poly(vinyl alcohol-vinyl acetate) copolymers, poly(vinyl alcohol-vinyl acetate-sodium vinyl sulfonate) copolymers; poly(vinyl pyrrolidone) and copolymer derivatives such as poly(vinyl pyrrolidone-vinyl acetate), poly(vinylpyrrolidone-vinyl alcohol), poly(vinylpyrrolidone-styrene); (ii) alkali-soluble polymers, e.g. poly(acrylic acid), poly(maleic acid), poly(alkyl (meth)acrylate-(meth)acrylic acid) copolymer, poly (acrylic acid-maleic acid)copolymer, poly(acrylamide), poly(methacrylic acid), poly((meth)acryl amide), (iii) poly(ethylene oxide) and poly(ethylene oxide-propylene oxide) block copolymers; (iv) mixtures thereof;
(5) Biodegradable (bio)polymers such as (i) polyesters, especially polymers of lactic, glycolic, hydroxybutyric acid derivatives such as poly (D,L-lactide), poly (L-lactide), poly (L-lactide-co-glycolide), poly(D,L-lactide-co-glycolide), poly (D,L-lactide-co-glycolide-D-glucose), poly (hydroxybutyric acid) and further derivatives, copolymers or mixtures thereof; (ii) water soluble or water dispersible forms of poly (3-hydroxy butyrate) derivatives; (iii) lignin derivatives such as lignosulphonates, oxylignins and kraft lignins and further derivatives or mixture thereof;
Preferred fragrance-encapsulating material is a mixture of modified starch bearing octenyl succinate moieties and mannitol, admixed in a weight % ratio of from 90:10 to from 10:90, particularly from 80:20 to 50:50.

By "protective coating" is meant a thin layer of a material having the function of preventing low levels of moisture present in the product causing breakdown or clumping of the particles, yet which, in the presence of larger amounts of water in use, will break down and allow release of the fragrance. Suitable protective coating materials are selected from cellulose, microcrystalline cellulose, cellulose ethers and esters such as ethyl cellulose, cellulose acetate, hydroxyethyl cellulose, hydroxypropyl methyl cellulose, hydroxypropyl methyl cellulose acetate, phthalate or succinate, as well as enteric/aquateric coatings and mixture thereof, carrageenan, chitosan, aceto-acetylated polyvinyl-alcohols, poly(alkyleneoxide) homopolymers and block copolymers, poly(vinylmethylether), poly(vinylether-maleic anhydride), organosilicones, and inorganic materials such as silicates, sulfates, borates, oxides, hydroxides, clay minerals, celites, zeolites in colloidal or powder form. The preferred protective coating is microcrystalline cellulose and hydroxyethyl cellulose, or a mixture thereof with carrageenan, maltodextrin and polyethylene glycol.

If color in the compositions be desired, it may be provided by the use of any suitable coloring matter. Coloring matters especially suitable for use in the present invention include water-soluble dyes and water-dispersible pigments having high affinity with the encapsulating material and, consequently, limited capability to migrate into the surroundings. It is preferred not to use coloring matters that migrate easily under the action of water, as these can lead to discoloration and staining of the composition, resulting in undesirable appearance, staining of the container or devices containing the composition, and staining of the environment surrounding the containers or devices should part of the composition be spilled out of these. It will be obvious to everybody skilled to the art that the selection of a suitable coloring matter will depend on the nature of the encapsulating material and that this selection relies on laboratory screening work. A convenient method of screening and selecting suitable coloring matters involves, for example, putting a colored particle of the delivery system on a bed of absorbent material, adding a certain amount of water (e.g. 1 ml) on to this particle and measuring the diameter of the colored spot which may result from coloring matter migration after a certain time (e.g. 24 hours). Coloring matters that generate colored spots with radius smaller than the average diameter of the colored particle are considered as suitable for the scope of the present invention. Preferred coloring matters are water-dispersible pigments such as phthalocyanine pigments. Most preferred colouring matters are aqueous dispersions of water-dispersible pigments formulated with styrene-acrylic resins.

The delivery system according to the present invention may contain formulation additives, such as emulsifiers, binders and anti-clumping agents, functional additives such as pH modifiers, and bioactive agents, such as anti microbial agents, insect repellent, and attractants.

The delivery system has a bulk density of 0.2-2.0, in particular, 0.4-2.0, 0.4-1.3, 0.5-1.5 and 0.7-1.1 g/cm$^3$, while the ratio of the bulk density of the delivery system to the bulk density of the external absorbent is between 0.5 and 1.5, particularly between 0.7 and 1.3 and more particularly between 0.8 and 1.2.

The delivery system is mixed with an external absorbent material. By "external absorbent material" is meant any free-flowing material that may absorb an aqueous liquid or a malodor in sufficient quantity to provide dampness and/or malodor control. Materials capable of absorbing more than 50% by weight of water or of decreasing substantially the headspace concentration and perception of malodor smell belong to the category of absorbent materials particularly useful in the present invention. It is considered as not relevant in the context of the present invention to make the difference between absorption and adsorption and, therefore, materials that are usually considered as adsorbent materials are included in the category of absorbent materials.

The free-flowing external absorbent may be particulate, for example, in the form of spherical or elongate particles, or fibrils. Typical external absorbent materials are selected, for example, from clays such as diatomaceous earth, sodium and calcium bentonites, sepiolites, illite and kaolinite; zeolites, aluminosilicates and porous or mesoporous silicates; cyclodextrins; activated charcoals; super-absorbing polymers such as polyacrylates, polyacrylamides or sulfonated polystyrene; organic absorbents such as ground corn cob, rice hull ash, ground alfalfa, cracked wheat, semolina, wood shavings, chopped soya bean stalk, peanut hull, wood shavings, and mixtures thereof. Mixtures of such absorbent materials with filler materials such as cellulose, sand, soil, ground rock, fly ash, or mixtures thereof, can be considered as absorbent materials, provided these mixtures exhibit appreciable water uptake and malodor absorbing properties as quoted above. Typically, the absorbent material is conditioned in order to improve its pourability, free flowability and aspect, to remove fine dusty particles and prevent excessive clumping in the presence of water. Typical conditioning treatments include but are not limited to granulation or agglomeration, compaction, extrusion and gasket extrusion, to provide granulated forms, beads, rods and flakes, which, optionally, can be admixed with anti-clumping agents. The methods of making these forms are well-known to the art.

In a specific embodiment of the present invention, especially useful in humidity absorbers and central air conditioning units, the absorbent material may be a known desiccant, such as calcium chloride, magnesium chloride, magnesium sulphate, silica gel, silicates, celite, activated alumina, zeolites, activated charcoals and molecular sieves. These may optionally be admixed with malodor-absorbing materials such as metal salts, for example, aluminium sulphate or zinc ricinoleate, cyclodextrins and activated charcoal.

In another specific embodiment of the present invention, especially useful in humidity absorbers and central air conditioning units, the composition is compressed in order to form a tablet or any compact shape that may be desirable.

A further possible ingredient of the external absorber is fragrance. Although in many cases, it is desirable to have all the fragrance in the delivery system, in some cases, it is desirable to have some fragrance, typically up to 1.0% by weight in the external absorber, preferably up to 0.5% by weight in the external absorber. The fragrance added to the external absorber need not be the same fragrance as used in the delivery system.

A preferred embodiment for animal litter is when the core material is an inorganic absorbent, especially when it is the same material as the external absorbent, as this has surprisingly been found to reduce clumping of the product. Preferred examples of core materials and external absorbents include diatomaceous earth, sodium and calcium bentonites, sepiolites and kaolinite, all optionally chemically treated.

The invention is also directed to a method of forming a delivery system as hereinabove described, comprising the steps of spraying a fragranced material on to an absorbent material, which thereby becomes the internal absorbent material as hereinabove described. Optionally, the resultant encapsulated material can be coated with a coating material as hereinabove defined.

The fragranced material may be sprayed on to particles, in the form of an emulsion, in order to build up compositions according to the invention. The fragranced material may be applied to the core particles in an agglomeration process, for example in a fluidised bed. Preferably, the agglomeration is carried out in any of the well-known fluidised bed dryers equipped with a product container. The process is started with the fluidisation of the core material.

The fragranced material emulsion may be formed by mixing under high shear the fragrance with an aqueous phase comprising water and the encapsulating materials, and optionally a dye to form an emulsion. The emulsion may thereafter be sprayed on to the fluidised core particles using a pressure, sonic or a pneumatic nozzle, preferably, a two-fluid nozzle, or a three-fluid nozzle which is inserted either on the top (top spray), lateral (lateral spray), tangential (tangential spray), or at the bottom (bottom spray) of the fluidised bed.

Alternatively, the fragranced material emulsion may be applied to the core particles in a spray coating process, wherein the fragranced material is coated on to a core material having a particle size and particle size distribution commensurate with the desired final delivery system particle size and particle size distribution. The spray coating process may be performed in a fluidised bed dryer, a drum coater, a pan coater or a Loedige mixer, or any mechanical device, where the particulate core material is put in motion in such a way that the surface of the particles is homogeneously exposed to the spray providing the atomized fragranced material emulsion.

After the agglomeration or spray coating process has been completed or after the emulsion has been completely sprayed on the fluidised core particles, the coating material can be optionally applied on the delivery system. Typically the coating material may be provided in the form of a melt, an aqueous solution, emulsion or dispersion and sprayed onto the delivery system using the same nozzle set-up as described above.

The present invention additionally provides an odor-control composition comprising typically:
0.1 to 10%, preferably 0.25-10%, more preferably 0.5 to 5% of fragrance delivery system, comprising
  50 to 90%, preferably 60 to 75%, of a core material and
  10 to 50%, preferably 25 to 40% of a fragranced material containing
    1 to 30%, preferably 10 to 20% of a fragrance or malodour-counteracting substance and
    70 to 99%, preferably 80 to 90% of fragrance encapsulating material,
  and, optionally,
    0.01 to 5%, preferably 0.2 to 2%, more preferably 0.2 to 2.5% of a dye
  and, optionally,
    0.5 to 10%, preferably 1 to 5% of protective coating material, optionally containing from 0.01 to 5%, preferably 0.2 to 2.5% of a dye;
and,
90 to 99.9%, preferably 90-99.75%, more preferably 95 to 99.5% of an external absorbent material; all percentages being by weight.

The composition and method of the present invention is useful in many different applications, in which malodors or the potential for their generation must be prevented or at least reduced. The invention therefore also provides a product that is adapted to be exposed to an actual or potential source of malodor and to at least reduce that malodor or potential therefore, the product comprising a solid, free-flowing composition as hereinabove defined.

The types of products in which the present invention can be used includes, but is not limited to, animal litters, sanitary towels and incontinence pads, filters for central air conditioning units, and humidity absorbers. The invention is particularly effective in conjunction with animal litters, especially those for cats. The invention therefore also provides an animal litter, especially a cat litter, comprising a solid, free-flowing composition as hereinabove defined.

The invention is now further described with reference to the following non-limiting examples, which describe preferred embodiments, all percentages of materials being by weight.

EXAMPLE 1

Preparation of Absorbent Material 800 g illite clay was poured into a Loedige laboratory wet granulator M 5 equipped with three ploughshare shovels attached to a rotating horizontal shaft, and a side-mounted spinning chopper.

The chamber was heated by external oil bath at 70° C. (product temperature was 55° C.).

100 ml water was directly added to the clay in the mixing chamber. The ploughshare and chopper were started and the mixing process was performed for 10 minutes. A further 50 ml water was added and it was mixed for 2 minutes. Finally 280 g 10% w/w hydroxypropyl methyl cellulose in water was pumped into the chamber.

The granulated material was dried in an oven at 80±5° C. for 20 minutes to yield a grey-brown granulated absorbent material of bulk density 1.03 g/cm$^3$.

EXAMPLE 2

Preparation of Delivery System with Absorbent as Core Material

A fragranced material emulsion was prepared by emulsifying 2 kg of fragrance oil into an aqueous phase containing 10 kg of water, 2 kg of mannitol 60 (ex Roquette Fréres), 6 kg of modified starch HiCap 100 (ex National Starch) and 0.07 kg of Heucosperse™ pigment GS dispersion (ex Heubach International) The emulsion was prepared according to a procedure wherein the aforementioned encapsulating materials were slowly added together under vigorous stirring (15500 rpm) with a polytron turbine (Ystral GmbH X 50710, Germany) until complete dissolution was reached. The fragrance was then added under continuous stirring. The mixture was homogenised for an additional 10 minutes until a stable emulsion was obtained having a mean particle size below 1 micron.

20 kg of the absorbent material prepared according to Example 1 was placed in a conical fluidised bed granulator WS-GT-0.40 (Allgaier Werke GmbH, Germany) and fluidized by applying a air flux of 300 m$^3$/h (as the process continued, it was found necessary to increase progressively the pressure to 600 m$^3$/h). 20 kg of said fragranced material emulsion was then sprayed on to the fluidized absorbent material by applying an atomisation air pressure of 2.5 bar with a spraying rate of up to 10 kg per hour, using a laterally-inserted two-fluid nozzle (Schlick Modell 0/2, Duesen-Schlick GmbH, Germany). The inlet temperature was 100° C., outlet temperature 45° C. Thereafter, an aqueous suspenion of coating material (LustreClear™ LC 101, ex FMC BioPolymer Pharmaceutical) was sprayed on to the resultant composition to form a coated granulated material containing 2% of coating material. This yielded 25 kg of delivery system in granulated form. After screening (2.0 mm sieve), the bulk density was found to be 0.90 g/cm$^3$, and the particulate material was dust-free and free-flowing.

EXAMPLE 3

Preparation of Delivery System with Sugar as Core Material

The same procedure was applied as above but the absorbent core material was replaced with saccharose Middling Fine (ex Südzucker, Germany) having a particle size distribution between 0.7 and 1.3 millimeters and a bulk density of 0.79 g/cm$^3$.

EXAMPLE 4

Preparation of Delivery System with Sugar as Core Material, by Spray Coating

A fragranced material emulsion containing 18.7% perfume, 8.4% mannitol 60 (ex Roquette Fréres), 33.6% Hi-Cap™ 100 (ex National Starch) and 0.1% of Heucosperse™ pigment dispersion (ex Heubach International) and 39.3% water was prepared as described in Example 1.

12 kg of coarse sugar core material (Carrare™ C10, ex Sucrerie Couplet, Belgium) was placed in a conical fluidised bed granulator WS-GT-0.40 (Allgaier Werke GmbH, Germany) and fluidized by applying a air flux of 350 m$^3$/h (as the process continued, it was found necessary to increase progressively the pressure to 600 m$^3$/h). 4.9 kg of said fragranced material emulsion was then sprayed on to coarse sugar by applying an atomisation air pressure of 4 bar with a spraying rate of up to 4 kg per hour, using a laterally-inserted two-fluid nozzle (Schlick Modell 0/2, Duesen-Schlick GmbH, Germany). The inlet temperature was 100° C., outlet temperature 45° C. This yielded a delivery system having particle size ranging from 2 mm to 3 mm and a bulk density of 0.74 g/cm$^3$, which was free-flowing and dust free.

EXAMPLE 5

Preparation of Delivery System with Corn Cob as Core Material, using a Drum Coater 1.25 kg corn cob fraction A1 (ex Independence Corn By-Products, Iowa, USA) was brought into a DRC Vario 500/600 (ex DRIAM, Germany) with a 2.5 L drum. Settings: distance bed—nozzle 8-10 cm; nozzle: 1.2 mm; Spray pressure: 1.0 bar; Spray rate: 5-12 g/min.

0.83 kg fragrance material emulsion comprising 39.5% water, 8.3% mannitol, 33.0% Hi-Cap™ 100, 18.6% perfume and 0.7% dye was sprayed using a Schlick three-fluid nozzle fed at 0.55 kg/h with a peristaltic pump. The inlet temperature was set on 80° C. and the outlet temperature at 50° C. during spraying.

Finally, 0.313 kg of a dispersion containing 8.0% LustreClear™ LC 101 (ex FMC BioPolymer Pharmaceutical) and 92% water was sprayed on the coloured product. The inlet temperature was hold at 80° C. and the outlet temperature at 45° C. during spraying.

This yielded 2.2 kg of delivery system having a bulk density of 0.56 g/cm$^3$, and the particulate material was dust-free and free-flowing.

EXAMPLE 6

Effect of Coating on Storage Stability

Various amounts of an aqueous suspension of coating material (LustreClear™ LC101, ex FMC BioPolymer Pharmaceutical) was sprayed on to the delivery system prepared according to Example 3. 1 g of delivery system, prepared according to example 3, was admixed with 49 g of absorbent material in an open Petri dish and placed under controlled climatic conditions (37° C. and 70% relative humidity for up to 5 weeks and 75° C. and 80% relative humidity for 1 day). After a certain period of time, as indicated in Table 1, the stickiness of the samples, i.e. the extent of clumping with neighbouring absorbent particles, was assessed. The samples were rated as follows: ++: not sticky, +: bit sticky, dust sticks, 0: slightly sticky, only small particles stick, −: sticky.

TABLE 1

| Sample Coating (%) | 37° C. and 70% RH | | | | 75° C. and 80% RH |
|---|---|---|---|---|---|
| | 1 day | 1 week | 3 weeks | 5 weeks | 1 day |
| 0.00 | 0 | – | – | – | – |
| 0.30 | + | + | 0 | – | – |
| 0.74 | ++ | + | – | – | 0 |
| 0.97 | ++ | + | – | – | 0 |
| 1.19 | ++ | ++ | – | – | 0 |
| 1.40 | ++ | ++ | + | – | 0 |
| 1.62 | ++ | ++ | + | – | 0 |
| 1.84 | ++ | ++ | +/0 | – | + |
| 2.06 | ++ | ++ | +/0 | – | + |
| 2.34 | ++ | ++ | +/0 | 0 | + |

EXAMPLE 7

Olfactive Evaluations in Litter

The fragrance delivery system as prepared in Example 2 contained 7% fragrance. This was dosed at 1%) into the absorbent material prepared in Example 1. An equivalent amount of free fragrance oil (0.07%) was dosed into the absorbent material prepared in example 1. 100 g of the respective mixtures was placed in 250 ml bottles. One set was compared initially for odor intensity by adding 10 g of water. A panel of 5 people rated the intensity of the odor on a 5 point scale (1=very low intensity of odor and 5=high intensity of odor). A second set was placed into a storage oven at 37 C for seven days. The samples were taken out of the oven and allowed to cool to room temperature. 10 g of water were poured on the respective products and the panel assessed them for odor intensity. The results were:

| Sample | Initial Intensity Rating | Intensity Rating - 7 days at 37 C. |
|---|---|---|
| Free Fragrance | 2.2 | 1.4 |
| Delivery System | 3.8 | 4.5 |

The delivery system is clearly highly efficient in retaining volatile fragrance ingredients over a prolonged period of time compared to adding the free fragrance oil.

EXAMPLE 8

Olfactive Evaluation of Different Particles

Using the process outlined in Example 3, two delivery systems were prepared. One had the internal sugar core material and a coating (2%) applied as described in Example 2. The second system had internal sugar core material but no coating was applied. The delivery systems were added at 1% to the absorbent material of prepared in Example 1 and samples prepared as per Example 5. A free fragrance control was prepared as in Example 5. The samples were evaluated using the methodology given in Example 5. The results of the panel were:

| Sample | Initial Intensity Rating | Intensity Rating - 7 days at 37 C. |
|---|---|---|
| Sugar-based delivery system with 2% coating | 3.8 | 4.0 |
| Sugar based delivery system | 4.0 | 4.6 |
| Free Fragrance | 2.2 | 1.4 |

EXAMPLE 9

Olfactive Evaluation of Different Particles in Bentonite Clay

The fragrance delivery system as prepared in Example 2. An enrobed system was prepared according to US patent 6,803,833 with the following recipe: 69 parts zeolite, 10 parts bentonite clay, 1 part propylene glycol, 20 parts fragrance.

Samples of the delivery system and the free fragrance were prepared as per Example 5. Samples containing the enrobed fragrance were prepared by adding 0.35% (w/w) to the clay to have equal fragrance. The samples were evaluated as per Example 5. The results are shown below:

| Sample | Initial Intensity Rating | Intensity Rating - 7 days at 37 C. |
|---|---|---|
| Delivery System Ex. 3 | 2.6 | 4.5 |
| Free Fragrance | 1.8 | 1.0 |
| Enrobed Fragrance | 2.8 | 3.4 |

The delivery system offers a performance benefit over the enrobed fragrance and a much larger one over the free fragrance after storage.

EXAMPLE 10

Effect of Internal Absorbent Core on Clumping

Using the process outlined in Examples 2, 3 and 5, three delivery systems were prepared. One had the internal clay absorbent without external coating. The second system had an internal sugar core material, no coating was applied. The third system had an internal corn cob core material, no coating was applied. The delivery systems were added at 1% to the external absorbent material prepared in Example 1 and samples stored at 30C and 80% relative humidity. The litters were assessed for clumping:

++=not sticky +=bit sticky dust sticks 0=bit sticky, small particles stick –=sticky.

The results are shown below:

| Sample | Degree of clumping |
|---|---|
| Internal clay core - No coating | + |
| Internal sugar core - no coating | – |
| Internal corn cob core - no coating | + |

The particles with an internal clay core clumped less than those with an internal sugar core.

EXAMPLE 11

Olfactive Evaluation of Delivery System in Incontinence Pads

The delivery system as prepared in Example 3 was added to Serenity® Extra absorbency incontinence pads manufactured by Tena. These pads were obtained as market samples. The incontinence pads were opened from the side and the inner absorbent layer separated to form a space for depositing the individual samples within. Two sets of samples were prepared by adding 0.3 g of the delivery system prepared according to Example 3 to the center of the pad for sample 1 and 0.0021 g of fragrance the center of a pad. Set 1 had 10 g of water added and the intensity paneled as per Example 5. Set 2 were placed in an oven at 37 C for 7 days the pads were equilibrated to room temperature and 10 g of water added to the respective pads. The results of the paneling were:

| Sample | Initial Intensity Rating | Intensity Rating - 7 days at 37 C. |
|---|---|---|
| Delivery System Ex. 2 | 2.9 | 4.2 |
| Free Fragrance | 4.0 | 1.0 |

Clearly the system is delivering more fragrance from the delivery system on storage.

The invention claimed is:

1. A solid, free-flowing composition adapted to deliver fragrance or malodor counteractant in a consumer product that is subjected to actual or potential malodorous influences, the solid, free-flowing composition comprising:
    a delivery system consisting of a particulate core material surrounded by a fragranced material comprising microdroplets of a fragrance dispersed in a fragrance-encapsulating material, wherein the delivery system is formed by applying a fragranced material emulsion, comprising the microdroplets dispersed in the fragrance-encapsulating material, to the particulate core material such that the outer surface of the particulate core material is homogeneously exposed to the fragranced material emulsion,
    optionally, surrounded by a protective coating,
    and,
    an external absorbent material in which the fragrance delivery system is dispersed.

2. The composition according to claim 1, consisting of
    the delivery system consisting of the core material surrounded by the fragranced material comprising the microdroplets of the fragrance dispersed in the fragrance-encapsulating material, surrounded by a protective coating,
    and,
    the external absorbent material in which the fragrance delivery system is dispersed.

3. The composition according to claim 1, in which both delivery system and external absorbent material are in free-flowing, granulated form, wherein the external absorbent material has particle sizes ranging from 0.2 to 10 millimeters and the delivery system has particle sizes ranging from 0.5 to 4 millimeters.

4. The composition according to claim 3, in which delivery system and external absorbent material are essentially spherical.

5. The composition according to claim 1, in which the delivery system has a bulk density of 0.4-2.0 g/cm$^3$.

6. The composition according to claim 1, in which the delivery system and the external absorbent material are of different colors.

7. The composition according to claim 1, in which the external absorbent material comprises fragrance.

8. The composition according to claim 1, in which there is present a protective coating selected from microcrystalline cellulose, hydroxyethyl cellulose, and a mixture thereof with carrageenan, maltodextrin and polyethylene glycol.

9. The composition according to claim 1, in which the absorbent material is a desiccant, this being optionally admixed with malodor-absorbing materials.

10. An odor-controlling composition comprising:
    0.1 to 10% of fragrance delivery system, comprising
        50 to 90% of a particulate core material and
        10 to 50% of a fragranced material formed from a fragranced material emulsion comprising
            1 to 30% of a fragrance or malodour-counteracting substance and
            70 to 99% of fragrance encapsulating material,
            wherein, wherein the fragranced material surrounds the particulate core material,
        wherein the fragrance delivery system is formed by applying the fragranced material emulsion, comprising microdroplets of the fragrance or malodour-counteracting substance dispersed in the fragrance encapsulating material, to the particulate core material such that the outer surface of the particulate core material is homogeneously exposed to the fragranced material emulsion
    and, optionally,
    0.01 to 5% of a dye
    and, optionally,
    0.5 to 10% of protective coating material, optionally containing from 0.01 to 5% of a dye;
    and,
    90 to 99.9% of an external absorbent material, all percentages being by weight.

11. The composition according to claim 3, in which the particle size of the external absorbent ranges from 0.5 to 5 millimeters.

12. The composition according to claim 3, in which the delivery system has particle sizes ranging from 1.5 to 3 millimeters.

13. The composition according to claim 3, in which the delivery system has particle sizes ranging from 0.8 to 3 millimeters.

14. The composition according to claim 5, in which the delivery system has a bulk density of 0.5-1.5g/cm$^3$.

15. The composition according to claim 5, in which the ratio of the bulk density of the delivery system to the bulk density of the external absorbent is between 0.5 and 1.5.

16. The composition according to claim 15, in which the ratio of the bulk density of the delivery system to the bulk density of the external absorbent is between 0.7 and 1.3.

17. The composition according to claim 16, in which the ratio of the bulk density of the delivery system to the bulk density of the external absorbent is between 0.8 and 1.2.

18. The composition according to claim 9, in which the desiccant is selected from the group consisting of calcium chloride, magnesium chloride, magnesium sulphate, silica gel, silicates, celite, activated alumina, zeolites, activated charcoals and molecular sieves.

19. The composition according to claim 9, in which the malodor-absorbing materials are selected from metal salts, cyclodextrins and activated charcoal.

20. A solid, free-flowing composition adapted to deliver fragrance or malodor counteractant in a consumer product that is subjected to actual or potential malodorous influences, the solid, free-flowing composition comprising:
    a delivery system consisting of a particulate core material surrounded by a fragranced material comprising microdroplets of a fragrance dispersed in a fragrance-encapsulating material, wherein the delivery system is formed by applying a fragranced material emulsion, comprising the microdroplets dispersed in the fragrance-encapsulating material, to the particulate core material such that the outer surface of the particulate core material is homogeneously exposed to the fragranced material emulsion, the fragrance-encapsulating material is selected from polysaccharides, modified polysaccharides and mannitol, a protective coating surrounding the delivery system, wherein the protective coating is selected from microcrystalline cellulose and hydroxyethyl cellulose and a mixture thereof with carrageenan, maltodextrin and polyethylene glycol, and, an external absorbent material in which the fragrance delivery system is dispersed.

* * * * *